United States Patent [19]

Shoesmith

[11] Plant 4,325

[45] Oct. 24, 1978

[54] CHRYSANTHEMUM NAMED AGGIE

[75] Inventor: Leonard H. Shoesmith, Westfield-Woking, England

[73] Assignee: Pan-American Plant Company, West Chicago, Ill.

[21] Appl. No.: 878,940

[22] Filed: Feb. 17, 1978

[51] Int. Cl.[2] ..... A01H 5/00

[52] U.S. Cl. ..... Plt./80

[58] Field of Search ..... Plt./79, 80

*Primary Examiner*—Robert E. Bagwill

*Attorney, Agent, or Firm*—Chas. W. Rummler

[57] ABSTRACT

A new variety of chrysanthemum plant characterized by the medium pink coloration of its medium size blooms of decorative flower form, its good performance as a spring, summer and fall potted plant and as a natural season garden plant with average garden chrysanthemum vigor. For glass house potted plant culture, this new variety has a 7-week photoperiodic response, a moderately spreading plant habit, good stem strength and medium sized but sparse foliage.

2 Drawing Figures

BACKGROUND OF THE NEW PLANT

This new plant originated as a seedling of unknown parentage grown at my breeding facilities at Westfield-Woking, Surrey, England, in 1973. This particular plant was selected by me for propagation and test because of the very attractive color of its blooms and its apparent adaptability to be grown as a garden chrysanthemum and accordingly I reproduced this plant at Westfield-Woking, Surrey, England, by means of cuttings from the original plant. Subsequent propagation of this new variety through successive generations, by means of vegetative cuttings, and careful observations of its growth and flowering characteristics, both at my aforesaid facilities in England and at West Chicago, Ill., U.S.A., has shown that all of its advantageous characteristics hereinafter set forth hold true from generation to generation and appear to be firmly fixed.

DESCRIPTION OF THE DRAWINGS

My new chrysanthemum variety is illustrated by the accompanying drawings, of which sheet one is a full color photographic rendition of a potted plant of this variety in full bloom, the colors shown being as nearly true as it is reasonably possible to obtain by conventional photographic procedures, the photograph having been made in November 1977; and sheet two is a mechanical print showing the configuration of typical leaves of this variety taken at various stages of maturity.

DESCRIPTION OF THE NEW PLANT

The following is a detailed description of my new chrysanthemum plant variety with the color designations according to the R.H.S. Colour Chart produced by The Royal Horticulture Society of London, England, in collaboration with the British Colour Council.

THE PLANT

Origin: Seedling.

Parentage: Unknown, this seedling having been found among plants resulting from random crosses.

Classification:

*Botanic.*—Chrysanthemum morifolium

*Commercial.*—Greenhouse pot chrysanthemum and outdoor garden chrysanthemum.

Form: Upright, perennial, herbaceous bush.

Height: About 19 to 48 cm.

Growth: Upright, vigorous and sturdy with average strength.

Branching: Average, under natural conditions.

Foliage: Quantity: Rather sparse with 5 to 7 leaves for each 10 cm. of stem length.

*Leaf size.*—About 5.6 to 11.0 cm. long and about 3.7 to 4.9 cm. in width. Shape: Lobed, lanceolate with slightly serrated margins. Surface aspect: Canescent. Color: Upper side: RHS 147A. Under side: RHS 147B. Venation: Pinnate. Petioles: About 1.6 to 2.8 cm. long.

THE BUD

Form: Elliptical.

Size: About 6 to 10 mm. in diameter and about 3 to 4 mm. in depth.

Opening rate: Slow.

Color:

*When phyllaries first divide.*—RHS 144A.

*When florets begin to unfurl.*—RHS 70B.

Phyllaries: The outside of the receptacle bears many involucral bracts which are spear-shaped and upstanding.

*Color.*—Inside: RHS 137A. Outside: RHS 137A.

*Surface texture.*—Pubescent.

Peduncle: Length: About 2.8 to 5.3 cm.

*Surface aspect.*—Pubescent.

*Strength.*—Erect.

THE FLOWER

Flowering characteristics: This variety can be flowered the year around with photoperiod control.

*Response.*—7-week.

*Recommended flowering.*—March 1 to November 1.

*Natural season flowering.*—September 26 to October 1.

Blooms: Flower type: Composite and decorative.

*Borne.*—A head of many florets borne on a receptacle.

*Size.*—Medium. Diameter: About 4.4 to 6.9 cm. Depth. About 1.8 to 2.6 cm.

*Shape.*—Cup-shaped when bloom first opens, acquiring a flat shape as bloom matures.

*Florets.*—Numerous in quantity. Form: Decorative. Appearance: Very slight shine.

*Color.*—

| | August | September | October | November |
|---|---|---|---|---|
| Outer Florets | | | | |
| Upper Side: | 74C | 74C | 74C | 74C, 74D |
| Reverse Side: | 73D | 73D | 69A | 73D |
| Inside Florets | | | | |
| Upper Side: | 74D | 70C | 74A, 73B | 74C, 72C, 73A |
| Reverse side: | 73D | 70D | 73D, 69A | 73D |

Tonality at distance of 2 meters: 9A: 72D, 73A, 73B

Peduncle: Sturdy and upright, about 2.8 to 5.3 cm. long. Color: RHS 147B.

Discoloration after full bloom: Moderate fading.

Persistence: Florets hang on and dry.

Fragrance: Typical chrysanthemum.

Lasting quality: 3 to 5 weeks on plant. Not recommended as a cut flower.

REPRODUCTIVE ORGANS

Stamens: Anthers: 5 syngenesious.

*Filaments.*—1 to 3 mm. long. Color: Light yellow.

Pollen.—Color: Yellow.

Pistils: Number: One to each ray and disc floret.

*Styles.*—Length: 3 to 5 mm.

*Stigmas.*—Color: Yellow.

Ovaries: Inferior bicarpellate.

This new variety of chrysanthemum plant is particularly characterized by the medium pink, medium sized blooms of decorative flower form and its substantially uniform 7-week photoperiodic response. This plant has good performance both as a potted plant for spring, summer and fall potted plant culture and as a natural season garden plant having average chrysanthemum vigor. The plant also has a moderately spreading plant habit, with good stem strength and medium sized but somewhat sparse foliage.

I claim:

1. A new variety of chrysanthemum plant, substantially as herein shown and described, characterized by the medium pink color of its blooms, its uniform flowering response and its good performance as a potted plant for spring, summer and fall culture and as a natural season garden plant having average garden chrysanthemum vigor.

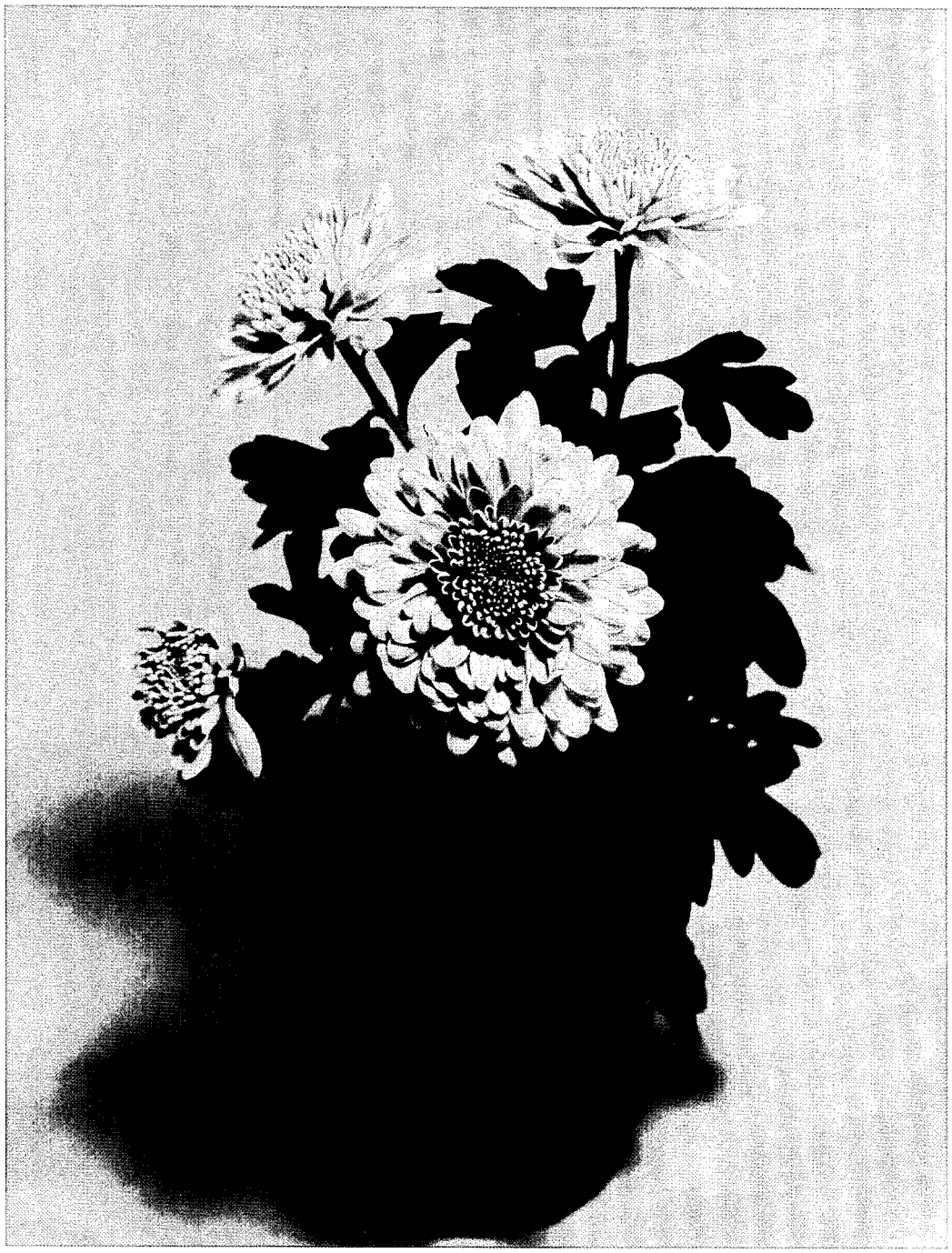

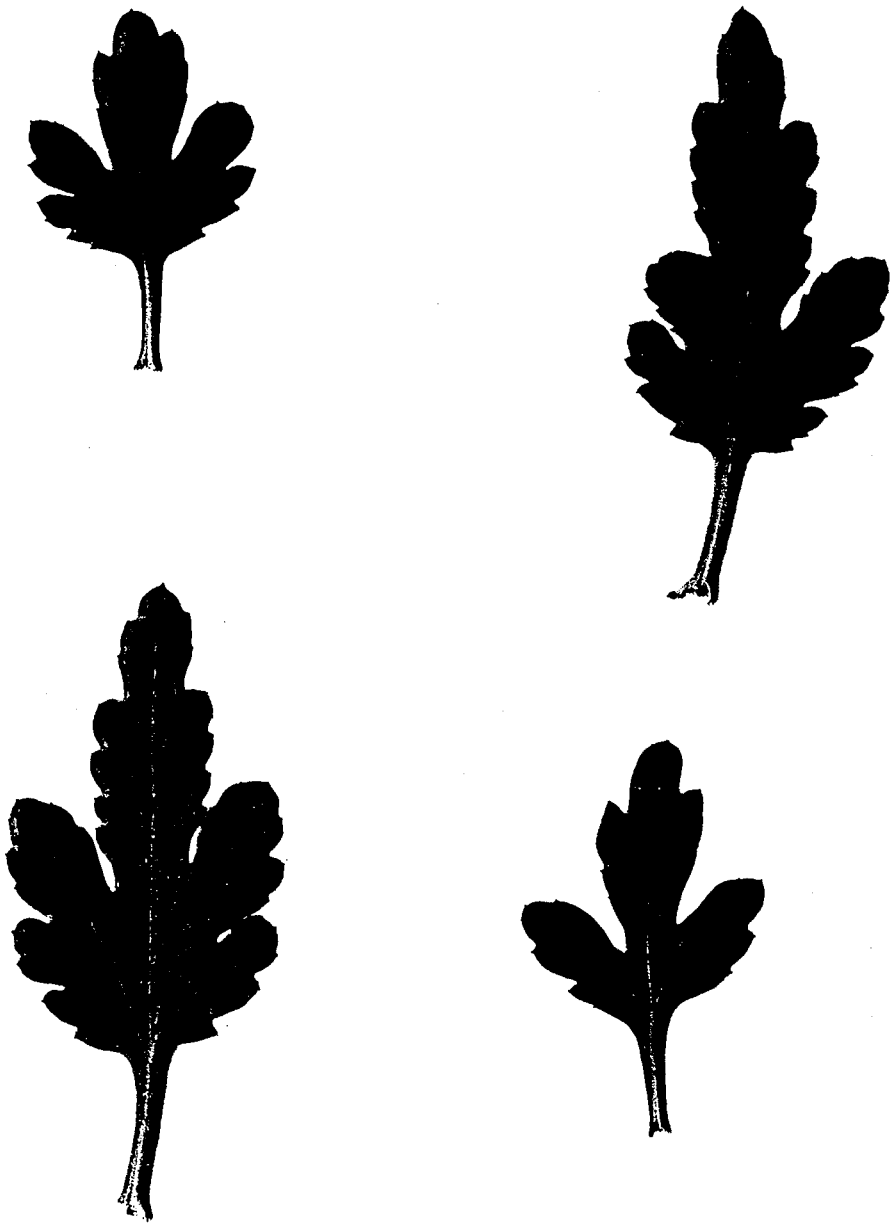

* * * * *